(12) United States Patent
Boiteau

(10) Patent No.: US 8,357,819 B2
(45) Date of Patent: Jan. 22, 2013

(54) METHOD FOR THE SYNTHESIS OF (Z)-3-[2-BUTOXY-3'-(3-HEPTYL-1-METHYL-UREIDO)-BIPHENYL-4-YL]-2-METHOXY-ACRYLIC ACID

(75) Inventor: Jean-Guy Boiteau, Saint-Aunes (FR)

(73) Assignee: Galderma Research & Development, Biot (FR)

( * ) Notice: Subject to any disclaimer, the term of this patent is extended or adjusted under 35 U.S.C. 154(b) by 452 days.

(21) Appl. No.: 12/599,647

(22) PCT Filed: Apr. 18, 2008

(86) PCT No.: PCT/FR2008/050706
§ 371 (c)(1),
(2), (4) Date: Jul. 6, 2010

(87) PCT Pub. No.: WO2008/139121
PCT Pub. Date: Nov. 20, 2008

(65) Prior Publication Data
US 2010/0286430 A1    Nov. 11, 2010

(30) Foreign Application Priority Data

May 11, 2007 (FR) ..................... 07 55021

(51) Int. Cl.
*C07C 273/18* (2006.01)
*C07C 309/65* (2006.01)
*C07C 309/73* (2006.01)
*C07C 309/63* (2006.01)
*C07C 69/732* (2006.01)

(52) U.S. Cl. ............... 558/44; 558/54; 560/60; 562/439

(58) Field of Classification Search .................. None
See application file for complete search history.

(56) References Cited

FOREIGN PATENT DOCUMENTS

WO    WO 2007/049158    5/2007

OTHER PUBLICATIONS

Brown et al., caplus an 1981:548694.*
Wuensch et al, caplus an 1995:766522.*
International Search Report for PCT/FR2008/050706, dated Dec. 10, 2008.
Ishiyama, et al., "Synthesis of Arylboronates via the Palladium(0)-Catalyzed Cross-Coupling Reaction of Tetra(alkoxo)diborons with Aryl Triflates," Tetrahedron Letters, 1997, 38, 19:3447-3450.
Nguyen et al., "The First General Palladium Catalyst for the Suzuki-Miyaura and Carbonyl Enolate Coupling of Aryl Arenesulfonates," J. Am. Chem. Soc. 2003, 125:11818-11819.
Suzuki, "Recent Advances in the Cross-Coupling Reactions of Organoboron Derivatives with Organic Electrophiles," 1995-1998, Journal of Organometallic Chemistry, 1999, 576:147-168.

* cited by examiner

*Primary Examiner* — Sun Jae Loewe
(74) *Attorney, Agent, or Firm* — Finnegan, Henderson, Farabow, Garrett & Dunner, LLP

(57) ABSTRACT

The invention relates to a process for the synthesis of (Z)-3-[2-butoxy-3'-(3-heptyl-1-methylureido)biphenyl-4-yl]-2-methoxyacrylic acid of formula (I):

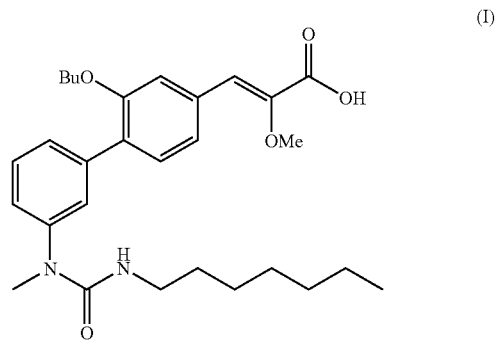

and also to the process for the synthesis of the reaction intermediates of general formula (XII), and to the said compounds when R2 is chosen from the methyl, trifluoromethyl, phenyl and 4-tolyl radicals:

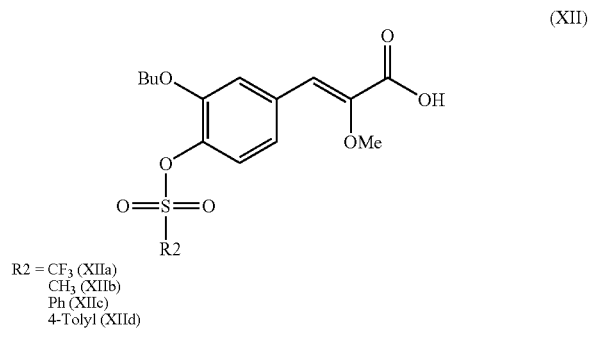

R2 = $CF_3$ (XIIa)
$CH_3$ (XIIb)
Ph (XIIc)
4-Tolyl (XIId)

19 Claims, 1 Drawing Sheet

METHOD FOR THE SYNTHESIS OF (Z)-3-[2-BUTOXY-3'-(3-HEPTYL-1-METHYL-UREIDO)-BIPHENYL-4-YL]-2-METHOXY-ACRYLIC ACID

This application is a national stage entry of International Application No. PCT/FR2008/050706, filed on Apr. 18, 2008, which claims priority to French Application No. FR 0755021, filed May 11, 2007.

The present invention relates to a novel process for the synthesis of (Z)-3-[2-butoxy-3'-(3-heptyl-1-methylureido) biphenyl-4-yl]-2-methoxyacrylic acid of formula (I):

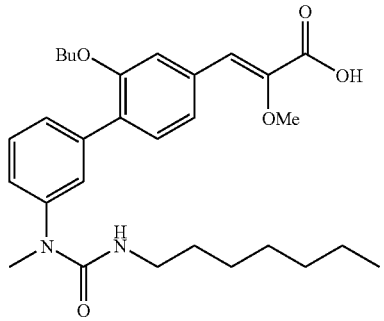
(I)

via the reaction intermediate of general formula (XII):

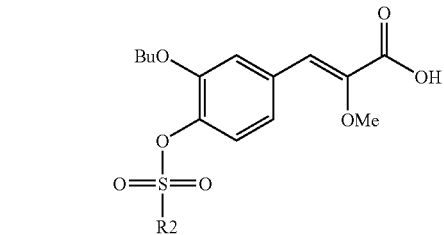
(XII)

R2 = CF₃ (XIIa)
CH₃ (XIIb)
Ph (XIIc)
4-Tolyl (XIId)

(Z)-3-[2-Butoxy-3'-(3-heptyl-1-methylureido)biphenyl-4-yl]-2-methoxyacrylic acid of formula (I) is a PPAR (peroxisome proliferator activated receptor) receptor modulator.

Figure 1:
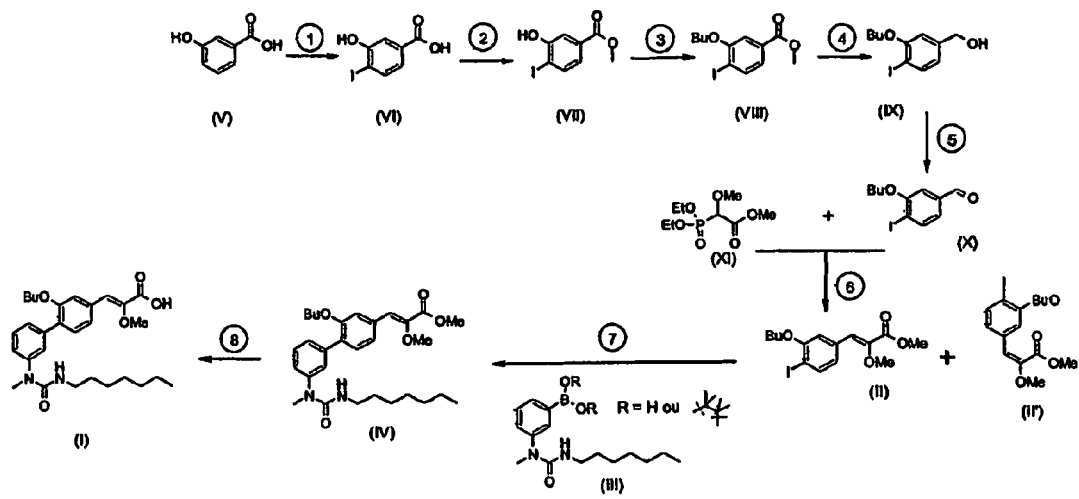

The synthesis of the compound of formula (I) was described in 8 stages in International Application WO2007/049158 and is as presented in FIG. 1:

Stage 1: 3-Hydroxybenzoic acid (V) is iodinated in the presence of sodium iodide and of sodium hypochlorite in order to give 4-iodo-3-hydroxybenzoic acid (VI).

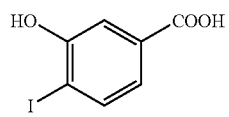
(VI)

Stage 2: 4-Iodo-3-hydroxybenzoic acid (VI) is esterified with methanol in the presence of sulphuric acid in order to provide methyl 3-hydroxy-4-iodobenzoate (VII).

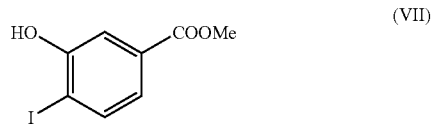 [SMILES: COC(=O)c1ccc(I)c(O)c1]
(VII)

Stage 3: The reaction between methyl 3-hydroxy-4-iodobenzoate (VII) and butyl iodide in the presence of potassium carbonate makes it possible to obtain methyl 3-butoxy-4-iodobenzoate (VIII).

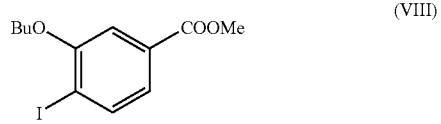
(VIII)

Stage 4: The compound (VIII) is subsequently reduced using lithium borohydride in order to give (3-butoxy-4-iodophenyl)methanol (IX).

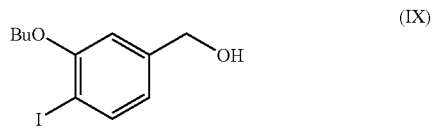
(IX)

Stage 5: The oxidation of (3-butoxy-4-iodophenyl)methanol (IX) using manganese dioxide makes it possible to obtain 3-butoxy-4-iodobenzaldehyde (X).

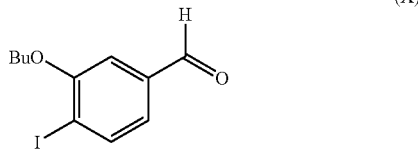
(X)

Stage 6: The Wittig reaction between 3-butoxy-4-iodobenzaldehyde (X) and methyl(diethoxyphosphoryl)-methoxyacetate (XI) in the presence of sodium hydride makes it possible to obtain a mixture of methyl (Z)-3-(3-butoxy-4-iodophenyl)-2-methoxyacrylate (II) and of methyl (E)-3-(3-butoxy-4-iodophenyl)-2-methoxyacrylate (II') in a 60/40 ratio. Methyl (Z)-3-(3-butoxy-4-iodophenyl)-2-methoxyacrylate (II) is obtained pure after chromatography on silica gel.

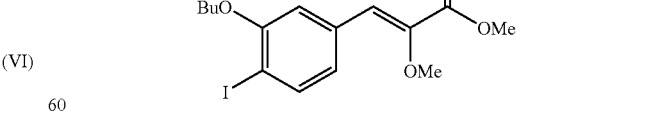
(II)

Stage 7: A palladium coupling reaction of Suzuki type is carried out between methyl (Z)-3-(3-butoxy-4-iodophenyl)-2-methoxyacrylate (II) and 3-(1-methyl-3-heptylureido)phenylboronic acid (III) in order to give methyl (Z)-3-[2-butoxy-3'-(3-heptyl-1-methylureido)-biphenyl-4-yl]-2-methoxyacrylate (IV).

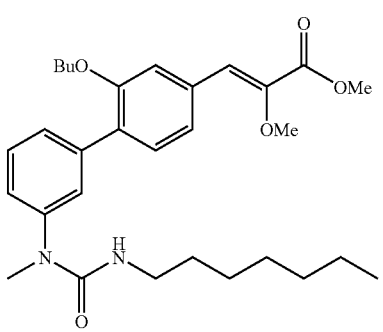

(IV)

Stage 8: A saponification reaction on methyl (Z)-3-[2-butoxy-3'-(3-heptyl-1-methylureido)biphenyl-4-yl]-2-methoxyacrylate (IV) using sodium hydroxide makes it possible to obtain (Z)-3-[2-butoxy-3'-(3-heptyl-1-methylureido)biphenyl-4-yl]-2-methoxyacrylic acid (I).

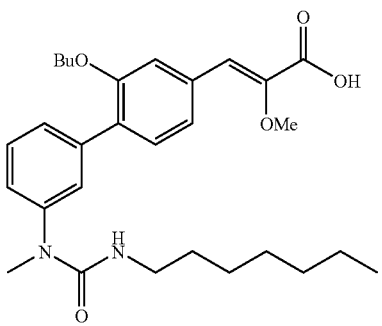

(I)

A first disadvantage of this synthetic route is the use of a lengthy linear reaction sequence in 8 stages between the commercial compound (V) and (Z)-3-[2-butoxy-3'-(3-heptyl-1-methylureido)biphenyl-4-yl]-2-methoxyacrylic acid (I). A linear synthesis is always unfavourable to an application on the industrial scale, for which a convergent synthesis will be preferred, in particular because of the search for a better yield.

Furthermore, the use of manganese dioxide also exhibits a disadvantage with regard to the industrial waste which it generates.

Finally, the separation of the two (Z) and (E) isomers of methyl 3-(3-butoxy-4-iodophenyl)-2-methoxyacrylate in stage 6, which employs a silica gel chromatography technique, is difficult to transfer to an industrial process.

Furthermore, the intermediate methyl (Z)-3-(3-butoxy-4-iodophenyl)-2-methoxyacrylate (II) in this process is a colourless oil, which can present problems of isolation in the transfer to the industrial scale.

Finally, the purification of (Z)-3-[2-butoxy-3'-(3-heptyl-1-methylureido)biphenyl-4-yl]-2-methoxyacrylic acid (I) in the synthetic route described above requires the use of three silica gel chromatography operations.

The present invention is thus targeted at solving the above-mentioned problems by providing a simplified process for the synthesis of (Z)-3-[2-butoxy-3'-(3-heptyl-1-methylureido)biphenyl-4-yl]-2-methoxyacrylic acid of formula (I) which comprises fewer stages, is more economical and is capable of being adapted to industrial synthesis.

Figure 2:
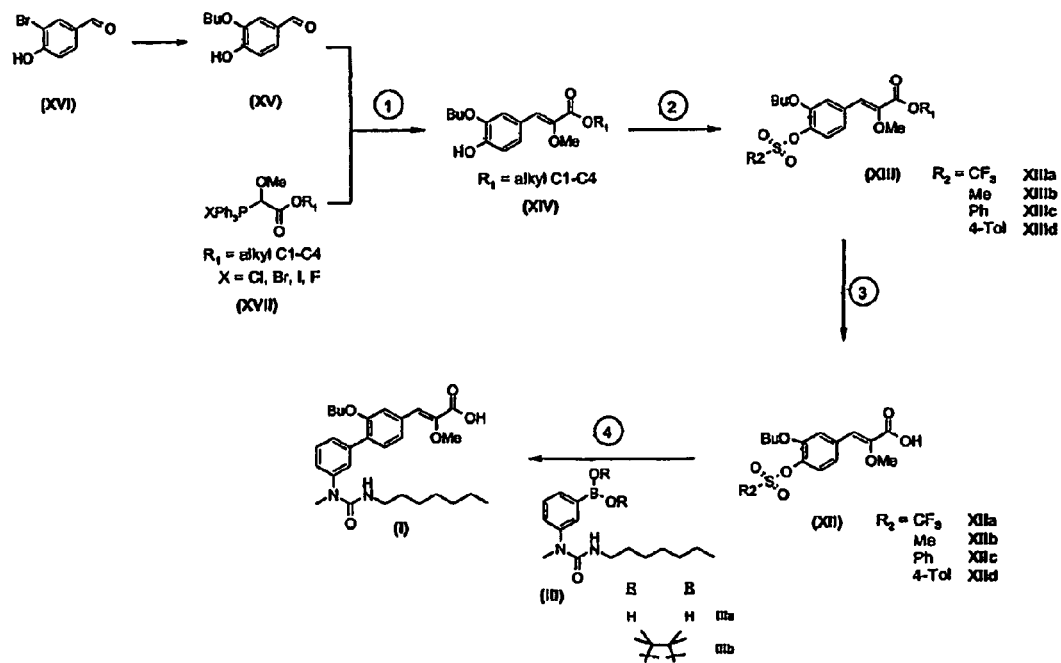

This is because the novel process for the synthesis of (Z)-3-[2-butoxy-3'-(3-heptyl-1-methylureido)biphenyl-4-yl]-2-methoxyacrylic acid (I), a subject-matter of the present invention, is a convergent synthesis comprising at most a linear sequence of 4 stages as presented in FIG. 2.

This novel process also makes it possible to prepare, in 3 stages, (Z)-3-(3-butoxy-4-(trifluoromethanesulphonyloxyphenyl)-2-methoxyacrylic acid of formula (XIIa) as reaction intermediate in the preparation of (Z)-3-[2-butoxy-3'-(3-heptyl-1-methylureido)biphenyl-4-yl]-2-methoxyacrylic acid (I).

The stages of the process according to the invention are as follows:

STAGE 1 OF THE PROCESS OF THE INVENTION

In a first stage, the novel synthetic process involves a Wittig reaction between (methoxy(alkoxycarbonyl)methyl)triphenylphosphonium halide (XVII) [prepared according to the process described in *Tetrahedron*, 1994, 50, 7543-7556] and 3-butoxy-4-hydroxybenzaldehyde (XV) [prepared by a coupling reaction between commercial 3-bromo-4-hydroxybenzaldehyde (XVI) and an alkali metal butoxide, such as sodium butoxide, for example, in the presence of copper(I) salt or of a palladium complex in a polar aprotic solvent, such as dimethylformamide (DMF), for example, at a temperature between 60° C. and 150° C. (The publication *Synth Commun.*, 1990, 20, 2659, describes similar reactions)] in the presence of an organic amine, such as triethylamine, for example, in an aprotic solvent, such as tetrahydrofuran (THF), for example, which makes it possible to obtain alkyl (Z)-3-(3-butoxy-4-hydroxyphenyl)-2-methoxyacrylate of general formula (XIV) where $R_1$ represents an alkyl radical. This procedure makes it possible to specifically obtain the (Z) isomer (>95%), which makes it possible, in contrast to the synthetic route described in International Application WO2007/049158, to dispense with any operation for the separation of Z/E isomers on silica gel.

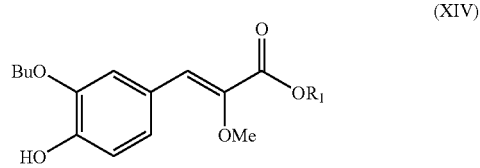

(XIV)

STAGE 2 OF THE PROCESS OF THE INVENTION

Alkyl (Z)-3-(3-butoxy-4-hydroxyphenyl)-2-methoxyacrylate (XIV) is reacted with triflic anhydride, for example, or mesyl chloride or benzenesulphonyl chloride or tosyl chloride in the presence of an organic base, such as, for example, triethylamine, in a solvent, such as dichloromethane, in order to respectively give alkyl (Z)-2-methoxy-3-(3-butoxy-4-(trifluoromethanesulphonyloxy)phenyl)acrylate (XIIIa) or alkyl (Z)-2-methoxy-3-(3-butoxy-4-(methanesulphonyloxy)phenyl)acrylate (XIIIb) or alkyl (Z)-2-methoxy-3-(3-butoxy-4-(phenylsulphonyloxy)phenyl)acrylate (XIIIc) or alkyl (Z)-2-methoxy-3-(3-butoxy-4-(tolylsulphonyloxy)phenyl)-acrylate (XIIId):

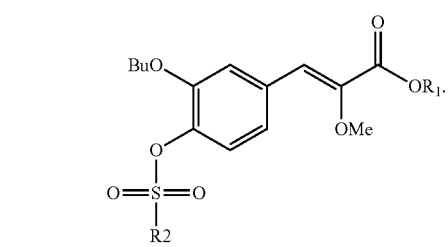

R₁ = alkyl radical
R2 = CF₃ (XIIa)
　　　CH₃ (XIIb)
　　　Ph (XIIc)
　　　4-Tolyl (XIId)

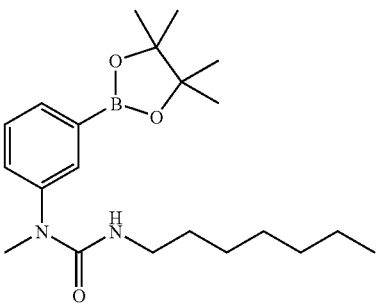

or its corresponding boronic acid (IIIa)

STAGE 3 OF THE PROCESS OF THE INVENTION

The saponification of the ester (XIII), for example alkyl (Z)-2-methoxy-3-(3-butoxy-4-(trifluoromethanesulphonyloxy)phenyl)acrylate (XIIIa), using a base, such as lithium hydroxide, for example, in a solvent, such as THF, for example, in the presence of water makes it possible to obtain (Z)-3-(3-butoxy-4-(trifluoromethanesulphonyloxy)phenyl)-2-methoxyacrylic acid (XIIa).

In the same way, the saponification starting from the esters (XIIIb), (XIIIc) or (XIIId) respectively results in the acids (XIIb), (XIIc) or (XIId).

The compound (IIIb) can be prepared in particular as described in International Application WO2007/049158, namely:

a—1-(3-Bromophenyl)-3-heptyl-1-methylurea (3-Bromophenyl)methylamine is prepared as follows:
150 g (500 mmol) of tert-butyl (3-bromophenyl)-N-methylcarbamate are placed in 600 ml of dichloromethane and 383 ml (5 mol) of trifluoroacetic acid. The reaction medium is stirred at ambient temperature for 24 hours, then treated with a saturated aqueous sodium carbonate solution and extracted with dichloromethane. The organic phase is washed with water, dried over magnesium sulphate, filtered and evaporated. 99 g (100%) of (3-bromophenyl)methylamine are obtained. Then:

3.2 ml (20 mmol) of heptyl isocyanate are added to a solution of 2.5 g (13 mmol) of (3-bromophenyl)methylamine, thus prepared, in 10 ml of tetrahydrofuran in the presence of 2 ml of triethylamine. The reaction mixture is stirred at ambient temperature for 12 hours. The reaction is halted by the addition of 2 ml of water and then extracted with ethyl acetate. The organic phases are combined and dried over sodium sulphate. The solvents are evaporated and then the residue is purified by chromatography on a column of silica eluted with a heptane/ethyl acetate 70/30 mixture. 3.4 g (77%) of 1-(3-bromophenyl)-3-heptyl-1-methylurea are obtained in the solid form.

b—3-Heptyl-1-methyl-1-[3-(4,4,5,5-tetramethyl-1,3,2-dioxaborolan-2-yl)phenyl]urea 4.0 g (15.5 mmol) of bis(pinacolato)diboron are added to a mixture of 3.4 g (10 mmol) of 1-(3-bromophenyl)-3-heptyl-1-methylurea and 3.0 g (31 mmol) of potassium acetate in the presence of 380 mg (0.5 mmol) of ((diphenylphosphino)ferrocene)palladium dichloride in 15 ml of dimethylformamide. The mixture is stirred at 90° C. for 3 hours. The reaction is

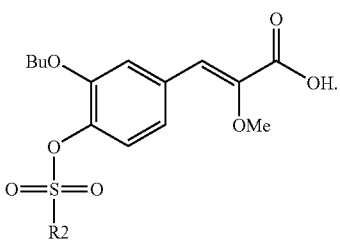

R2 = CF₃ (XIIa)
　　　CH₃ (XIIb)
　　　Ph (XIIc)
　　　4-Tolyl (XIId)

STAGE 4 OF THE PROCESS OF THE INVENTION

Stage 4 of the process which is a subject-matter of the present invention consists of the synthesis of (Z)-3-[2-butoxy-3'-(3-heptyl-1-methylureido)biphenyl-4-yl]-2-methoxyacrylic acid of formula (I) by a coupling reaction, preferably catalyzed with palladium or with nickel, between, for example, (Z)-3-(3-butoxy-4-(trifluoromethanesulphonyloxy)phenyl)-2-methoxyacrylic acid (XIIa) and 3-heptyl-1-methyl-1-[3-(4,4,5,5-tetramethyl-1,3,2-dioxaborolan-2-yl)phenyl]urea (IIIb)

halted by the addition of 50 ml of water and then extracted with ethyl acetate. The organic phases are combined and dried over sodium sulphate. The solvents are evaporated and then the residue is purified by chromatography on a column of silica eluted with a heptane/ethyl acetate 70/30 mixture. 2.5 g (64%) of 3-heptyl-1-methyl-1-[3-(4,4,5,5-tetramethyl-1,3,2-dioxaborolan-2-yl)phenyl]urea (IIIb) are obtained in the form of an oil.

The compound (IIIa) is, for its part, also prepared as described in International Application WO2007/049158, namely:

a—1-(3-Bromophenyl)-3-heptyl-1-methylurea:
Procedure identical to that described above.

b—3-(3-Heptyl-1-methylureido)phenylboronic acid:
The reaction of 113 g (345 mmol) of 1-(3-bromophenyl)-3-heptyl-1-methylurea in 1.1 l of tetrahydrofuran, 127 ml (380 mmol) of a 1.6M solution of methyllithium in diethyl ether, 530 ml (760 mmol) of a 1.7M solution of tert-butyllithium in pentane and 97 ml (904 mmol) of trimethyl borate results in 36 g (36%) of 3-(3-heptyl-1-methylureido)phenylboronic acid (IIIa) in the form of a pink powder after purification of the crude residue by chromatography on silica gel eluted with heptane/ethyl acetate 50/50 mixture and crystallization from an ethyl acetate/heptane mixture.

In the same way, the coupling reaction starting from the acids (XIIb), (XIIc) or (XIId) (acids of formula (XII) for which R2 represents a methyl group, a phenyl group or a tolyl group) results in (Z)-3-[2-butoxy-3'-(3-heptyl-1-methylureido)biphenyl-4-yl]-2-methoxyacrylic acid of formula (I).

(Z)-3-[2-Butoxy-3'-(3-heptyl-1-methylureido)biphenyl-4-yl]-2-methoxyacrylic acid of formula (I) is purified by recrystallization from diisopropyl ether, a technique which can be transferred to the industrial scale.

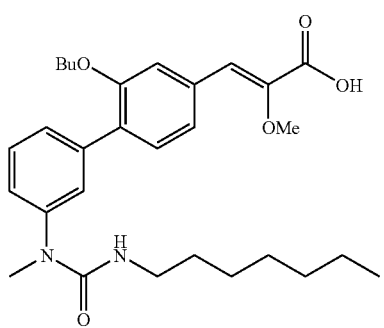

(I)

The coupling conditions of this final stage are well known to a person skilled in the art. The latter, in the context of the present invention, can use both conventional coupling conditions (see A. Suzuki et al., *Synth. Commun.*, 1981, 11, 513, or Sharp, M. J., *Tet. Lett.*, 1985, 26, 5997) and optimized conditions (see, for example, Littke, A. F. et al., *J. Am. Chem. Soc.*, 2000, 122 (17), 4020-4028). The embodiment described below involves a nonexclusive choice of conditions.

According to the present invention, alkyl denotes a saturated linear or branched hydrocarbon chain comprising from 1 to 4 carbon atoms. Preferably, such a radical is chosen from the methyl, ethyl, propyl, butyl, isopropyl and t-butyl radicals.

According to the present invention, alkoxy denotes an oxygen atom substituted by a saturated linear or branched hydrocarbon chain comprising from 1 to 4 carbon atoms.

According to the present invention, alkoxycarbonyl denotes a carbonyl substituted by an alkoxy as defined above.

According to the present invention, halogen denotes a chlorine, fluorine, bromine or iodine atom.

The present invention also relates to the various reaction intermediates employed in the process of the invention, namely:

the sulphonates of general formula (XII) where R2 is chosen from a methyl group, a trifluoromethyl group, a phenyl group and a tolyl group, represented by (Z)-3-(3-butoxy-4-(trifluoromethanesulphonyloxy)-phenyl)-2-methoxyacrylic acid (XIIa), (Z)-3-(3-butoxy-4-(methanesulphonyloxy)phenyl)-2-methoxyacrylic acid (XIIb), (Z)-3-(3-butoxy-4-(phenylsulphonyloxy)phenyl)-2-methoxyacrylic acid (XIIc) and (Z)-3-(3-butoxy-4-(tolylsulphonyloxy)phenyl)-2-methoxyacrylic acid (XIId):

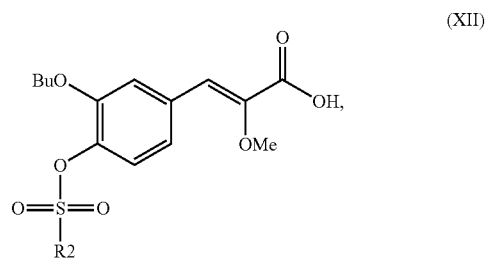

(XII)

R2 = CF₃ (XIIa)
    CH₃ (XIIb)
    Ph (XIIc)
    4-Tolyl (XIId)

the sulphonates of general formula (XIII) in which $R_1$ represents an alkyl radical and R2 represents a methyl group, a trifluoromethyl group, a phenyl group or a tolyl group, represented by alkyl (Z)-2-methoxy-3-(3-butoxy-4-(trifluoromethanesulphonyloxy)-phenyl)acrylate (XIIIa), alkyl (Z)-2-methoxy-3-(3-butoxy-4-(methanesulphonyloxy)phenyl)acrylate (XIIIb), alkyl (Z)-2-methoxy-3-(3-butoxy-4-(phenylsulphonyloxy)-phenyl)acrylate (XIIIc) and alkyl (Z)-2-methoxy-3-(3-butoxy-4-(tolylsulphonyloxy)phenyl)acrylate (XIIId)

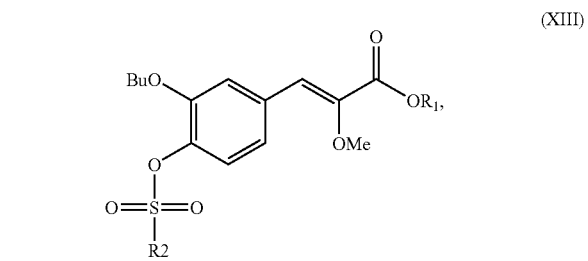

(XIII)

$R_1$ = alkyl radical
R2 = CF₃ (XIIIa)
    CH₃ (XIIIb)
    Ph (XIIIc)
    4-Tolyl (XIIId)

alkyl (Z)-3-(3-butoxy-4-hydroxyphenyl)-2-methoxyacrylate (XIV) where $R_1$ is an alkyl radical:

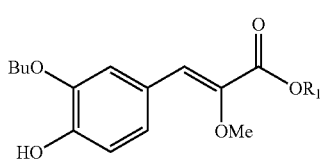
(XIV)

Other characteristics and advantages of the present invention will become more apparent on reading the procedure below, given by way of illustration and without implied limitation.

Preparation of the Starting Materials

3-Butoxy-4-hydroxybenzaldehyde (XV)

2.16 g (93.9 mmol) of sodium are dissolved in 15 ml of n-butanol at 110° C. for 3 hours. 20 ml of dimethylformamide are added at ambient temperature and then the medium is degassed several times. 3.4 g (34.1 mmol) of copper(I) chloride are added at ambient temperature and then the reaction medium is stirred for 10 minutes. 6.2 g (31 mmol) of 3-bromo-4-hydroxybenzaldehyde are added and then the reaction medium is stirred at 120° C. for 2 hours. The reaction mixture is cooled to ambient temperature and then the reaction is halted by the addition of 50 ml of a 2M hydrochloric acid solution. The medium is extracted with 250 ml of ethyl acetate. The solvents are evaporated and then the residue is filtered through a silica gel patch (2 cm): eluent heptane/ethyl acetate 8/2. After evaporation of the solvents, 5.55 g of orange oil are obtained. This oil is crystallized from pentane. 4.8 g of 3-butoxy-4-hydroxybenzaldehyde are obtained in the form of a brown solid after filtration.

Yield=80%.

$^1$H NMR (400 MHz, $CDCl_3$): 0.99 (t, J=8 Hz, 3H, $CH_2$); 1.52 (hex, J=8 Hz, 2H, $CH_2$); 1.85 (pent, J=8 Hz, 2H, $CH_2$); 4.14 (t, J=8 Hz, 2H, $CH_2$); 6.24 (s, 1H, ArH); 7.05 (d, J=8 Hz, 1H, ArH); 7.42 (m, 2H, ArH+OH); 9.83 (s, 1H, CHO).

(Methoxy(methoxycarbonyl)methyl)triphenylphosphonium chloride (XVII)

25 g (0.186 mol) of methyl dimethoxyacetate are added to 27 ml (0.215 mol) of acetyl chloride at ambient temperature. 0.1 g (0.2 mol %) of diiodine are added and then the reaction mixture is stirred at 55° C. for 16 hours. The excess acetyl chloride is evaporated under vacuum and then the residue is dissolved in 100 ml of dichloromethane. 49 g (0.204 mol) of triphenylphosphine are added and then the reaction mixture is stirred at 37° C. for 3 hours. The solvents are evaporated and then the residue is crystallized from diisopropyl ether. 70 g of (methoxy(methoxycarbonyl)methyl)triphenylphosphonium chloride are obtained.

Yield=88%.

$^1$H NMR (400 MHz, $CDCl_3$) 3.61 (s, 3H, $OCH_3$); 3.90 (s, 3H, $OCH_3$); 7.66 (m, 6H, ArH), 7.77 (m, 3H, ArH); 8.01 (m, 6H, ArH); 8.71 (d, J=13 Hz, 1H, CH).

Stages of the Process

STAGE 1 Methyl (Z)-3-(3-butoxy-4-hydroxyphenyl)-2-methoxyacrylate (XIV)

4.0 g (20.6 mmol) of 3-butoxy-4-hydroxybenzaldehyde and 13.25 g (30.9 mmol) of (methoxy(methoxycarbonyl)methyl)triphenylphosphonium chloride are suspended in 40 ml of tetrahydrofuran. 6 ml (42 mmol) of triethylamine are added and then the reaction medium is stirred at 40° C. for 16 hours. The reaction medium is filtered and then the solvents are evaporated. 50 ml of diethyl ether are added and the mixture is stirred at ambient temperature for 10 minutes and then filtered. After evaporation of the solvents, the residue is taken up in a heptane/ethyl acetate 8/2 mixture and then filtered through a silica patch (2 cm). 5.3 g of methyl (Z)-3-(3-butoxy-4-hydroxyphenyl)-2-methoxyacrylate are obtained after evaporation of the solvents.

Yield=92%.

$^1$H NMR (400 MHz, $CDCl_3$): 0.91 (t, J=8 Hz, 3H, $CH_3$); 1.42 (hex, J=8 Hz, 2H, $CH_2$); 1.75 (pent, J=8 Hz, 2H, $CH_2$); 3.66 (s, 3H, $OCH_3$); 3.78 (s, 3H, $OCH_3$); 4.00 (t, J=8 Hz, 2H, $CH_2$); 5.79 (s, 1H, CH=); 6.84 (d, J=8 Hz, 1H, ArH), 6.88 (s, 1H, ArH); 7.13 (d, J=8 Hz, 1H, ArH); 7.39 (s, 1H, OH).

STAGE 2: Methyl (Z)-2-methoxy-3-(3-butoxy-4-(trifluoromethanesulphonyloxy)phenyl)acrylate 2.6 g (9.27 mmol) of methyl (Z)-3-(3-butoxy-4-hydroxyphenyl)-2-methoxyacrylate are dissolved in 25 ml of dichloromethane and then 2 ml of triethylamine are added. 1.67 ml of triflic anhydride (10.2 mmol) are slowly added at 0° C. The reaction mixture is stirred at 0° C. for 2 hours. The reaction is halted using a saturated sodium hydrogencarbonate solution. The medium is extracted with ethyl acetate. The organic phases are combined, dried over sodium sulphate and then filtered through a silica patch (1 cm). The solvents are evaporated. 3.57 g of methyl (Z)-2-methoxy-3-(3-butoxy-4-(trifluoromethanesulphonyloxy)phenyl)acrylate are obtained.

Yield=93%.

$^1$H NMR (400 MHz, $CDCl_3$): 0.91 (t, J=7 Hz, 3H, $CH_3$); 1.46 (hex, J=7 Hz, 2H, $CH_2$); 1.76 (pent, J=7 Hz, 2H, $CH_2$); 3.73 (s, 3H, $OCH_3$); 3.80 (s, 3H, $OCH_3$); 4.00 (t, J=7 Hz, 2H, $CH_2$); 6.83 (s, 1H, CH=); 7.11 (d, J=8 Hz, 1H, ArH); 7.20 (d, J=8 Hz, 1H, ArH); 7.45 (s, 1H, ArH)

STAGE 3: (Z)-3-(3-Butoxy-4-(trifluoromethanesulphonyloxy)phenyl)-2-methoxyacrylic acid (XIIa)

1.53 g (36.3 mmol) of lithium hydroxide monohydrate are added to a solution of 7.5 g (18.2 mmol) of methyl (Z)-2-methoxy-3-(3-butoxy-4-(trifluoromethanesulphonyloxy)phenyl)acrylate in 50 ml of a tetrahydrofuran/water 10/1 mixture. The reaction mixture is stirred at 68° C. for 5 hours. The reaction mixture is acidified with a 2N hydrochloric acid solution down to pH=1. The reaction mixture is extracted with two times 100 ml of a heptane/ethyl acetate 1/2 mixture. The organic phases are combined and then dried over sodium sulphate. The solvents are evaporated and then the residue is taken up in 30 ml of pentane. 4.7 g of (Z)-3-(3-Butoxy-4-(trifluoromethane-sulphonyloxy)phenyl)-2-methoxyacrylic acid are obtained in the form of a white solid.

Yield=63%.

$^1$H NMR (400 MHz, $CDCl_3$): 1.00 (t, J=7 Hz, 3H, $CH_3$); 1.56 (hex, J=7 Hz, 2H, $CH_2$); 1.86 (pent, J=7 Hz, 2H, $CH_2$); 3.86 (s, 3H, $OCH_3$); 4.10 (t, J=7 Hz, 2H, $CH_2$); 7.07 (s, 1H, CH=); 7.23 (d, J=8 Hz, 1H, ArH); 7.33 (d, J=8 Hz, 1H, ArH); 7.56 (s, 1H, ArH)

STAGE 4 (Z)-3-[(2-Butoxy-3'-(3-heptyl-1-methylureido)biphenyl-4-yl]-2-methoxyacrylic acid (I)

870 g (2.2 mmol) of (Z)-3-(3-butoxy-4-(trifluoromethane-sulphonyloxy)phenyl)-2-methoxyacrylic acid (XII), 981 mg (2.62 mmol) of 3-heptyl-1-methyl-1-[3-(4,4,5,5-tetramethyl-1,3,2-dioxaborolan-2-yl)phenyl]urea (III) [prepared according to International Application WO2007/049158], 14 mg (3 mol %) of palladium acetate and 46 mg (6 mol %) of dicyclohexylbiphenylphosphine are dissolved in 8 ml of dimethylformamide, 1.5 ml of a 2M potassium phosphate solution are added and the medium is degassed several times. The reaction mixture is stirred at 90° C. for 2 hours. The reaction is halted with a 2M hydrochloric acid solution and then the mixture is extracted with ethyl acetate. The organic phases are washed with a sodium chloride solution and then dried over Na$_2$SO$_4$. The solvents are evaporated and then the residue is taken up in 10 ml of heptane/AcOEt 1/1. Filtration is carried out through a silica patch (1 cm). The solvents are evaporated. The residue is precipitated from pentane. The solid is recrystallized from isopropyl ether/heptane. 510 mg of (Z)-3-[2-butoxy-3'-(3-heptyl-1-methylureido)biphenyl-4-yl]-2-methoxyacrylic acid are obtained in the solid form.

Yield=47%.

Melting point=99° C.

$^1$H NMR (400 MHz, CDCl$_3$): 0.85 (t, J=7 Hz, 3H, CH$_3$); 0.95 (t, J=7 Hz, 3H, CH$_3$); 1.24 (m, 8H, CH$_2$); 1.42 (m, 4H, CH$_2$); 1.78 (m, 2H, CH$_2$); 3.18 (td, J=7 Hz, J=6 Hz, 2H, NCH$_2$); 3.33 (s, 3H, NCH$_3$); 3.89 (s, 3H, OCH$_3$); 4.05 (t, J=7 Hz, 2H, OCH$_2$); 4.46 (t, J=6 Hz, 1H, NH); 7.17 (s, 1H, =CH); 7.23 (d, J=8 Hz, 1H, ArH); 7.35-7.54 (m, 6H, ArH).

I claim:

1. A process for the synthesis of (Z)-3-[2-butoxy-3'-(3-heptyl-1-methylureido)biphenyl-4-yl]-2-methoxyacrylic acid of formula (I)

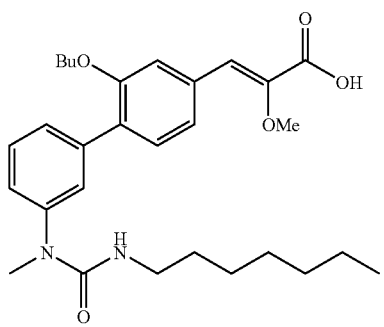
(I)

comprising reacting a sulphonate of formula (XII):

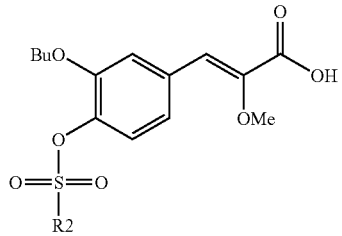
(XII)

in which R2 is chosen from a methyl radical, a trifluoromethyl radical, a phenyl radical and a tolyl radical,
with at least one boron-comprising entity chosen from 3-heptyl-1-methyl-1-[3-(4,4,5,5-tetramethyl-1,3,2-dioxoborolan-2-yl)phenyl]urea of formula (IIIb)

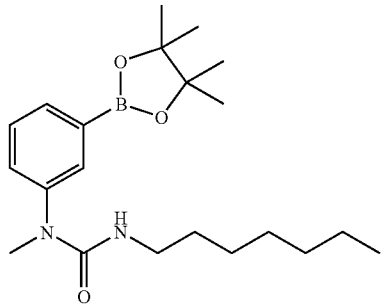
(IIIb)

and its corresponding boronic acid of formula (IIIa)

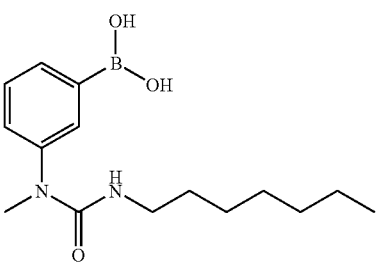
(IIIa)

2. The process of claim 1, wherein the reacting is carried out in the presence of at least one catalyst chosen from palladium and nickel catalysts.

3. The process of claim 1, wherein the sulphonate of formula (XII)

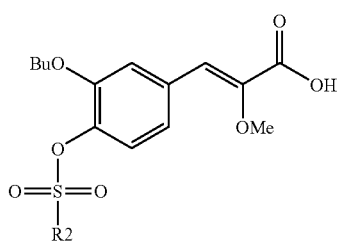
(XII)

is obtained by saponifying an ester of formula (XIII)

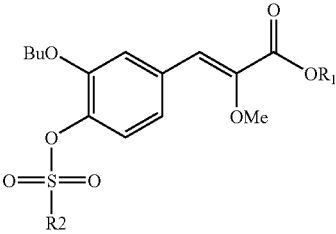
(XIII)

in which R$_1$ is chosen from alkyl radicals.

4. The process of claim 3, wherein the ester of formula (XIII):

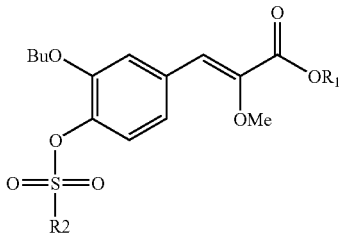

(XIII)

is obtained by reacting an alkyl (Z)-3-(3-butoxy-4-hydroxyphenyl)-2-methoxyacrylate of formula (XIV):

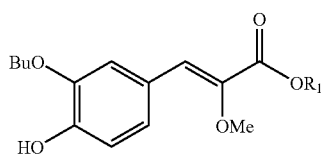

(XIV)

in which $R_1$ is chosen from alkyl radicals,
with an electrophile chosen from triflic anhydride, mesyl chloride, benzenesulphonyl chloride and tosyl chloride.

5. The process of claim 4, wherein the alkyl (Z)-3-(3-butoxy-4-hydroxyphenyl)-2-methoxyacrylate of formula (XIV):

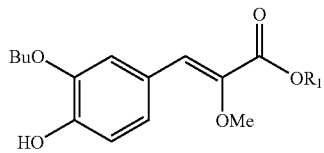

(XIV)

is obtained by carrying out a Wittig reaction between 3-butoxy-4-hydroxybenzaldehyde of formula (XV):

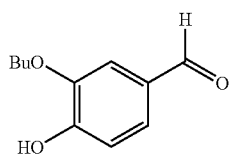

(XV)

and a (methoxy(alkoxycarbonyl)methyl)triphenylphosphonium halide of formula (XVII):

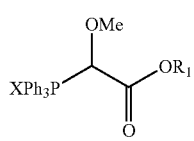

(XVII)

in which $R_1$ is chosen from alkyl radicals and X is chosen from halogens.

6. The process of claim 5, wherein X is chloride.

7. The process of claim 4, wherein the electrophile is triflic anhydride.

8. The process of claim 3, wherein $R_1$ is a methyl radical.

9. The process of claim 1, wherein R2 is a trifluoromethyl radical.

10. The process of claim 1, wherein the at least one boron-comprising entity is 3-heptyl-1-methyl-1-[3-(4,4,5,5-tetramethyl-1,3,2-dioxoborolan-2-yl)phenyl]urea.

11. At least one chemical entity of formula (XIII):

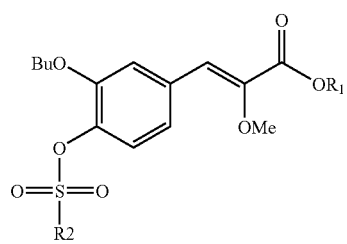

(XIII)

in which $R_1$ is chosen from hydrogen and alkyl radicals, and R2 is chosen from a methyl radical, a trifluoromethyl radical, a phenyl radical and a tolyl radical.

12. The at least one chemical entity of claim 11, wherein $R_1$ is hydrogen.

13. The at least one chemical entity of claim 12, wherein R2 is a trifluoromethyl radical.

14. The at least one chemical entity of claim 11, wherein $R_1$ is chosen from alkyl radicals.

15. The at least one chemical entity of claim 14, wherein R2 is a trifluoromethyl radical.

16. The at least one chemical entity of claim 14, wherein $R_1$ is a methyl radical.

17. The at least one chemical entity of claim 16, wherein R2 is a trifluoromethyl radical.

18. At least one chemical entity chosen from alkyl (Z)-3-(3-butoxy-4-hydroxyphenyl)-2-methoxyacrylates of formula (XIV):

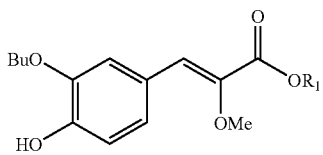

(XIV)

in which $R_1$ is chosen from alkyl radicals.

19. The at least one chemical entity of claim 18, wherein $R_1$ is a methyl radical.

* * * * *